(12) United States Patent
Irisawa

(10) Patent No.: US 9,649,034 B2
(45) Date of Patent: May 16, 2017

(54) PHOTOACOUSTIC IMAGING APPARATUS AND METHOD FOR OPERATING A PHOTOACOUSTIC IMAGING APPARATUS

(71) Applicant: FUJIFILM Corporation, Minato-ku, Tokyo (JP)

(72) Inventor: Kaku Irisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 483 days.

(21) Appl. No.: 13/871,547

(22) Filed: Apr. 26, 2013

(65) Prior Publication Data

US 2013/0237802 A1    Sep. 12, 2013

Related U.S. Application Data

(63) Continuation of application No. PCT/JP2011/005843, filed on Oct. 19, 2011.

(30) Foreign Application Priority Data

Oct. 27, 2010 (JP) ................ 2010-240696
Oct. 17, 2011 (JP) ................ 2011-227678

(51) Int. Cl.
*A61B 5/05*       (2006.01)
*A61B 5/00*       (2006.01)
(Continued)

(52) U.S. Cl.
CPC ........ *A61B 5/0095* (2013.01); *A61B 5/14532* (2013.01); *A61B 5/14551* (2013.01)

(58) Field of Classification Search
USPC ........................................................ 600/407
See application file for complete search history.

(56) References Cited

U.S. PATENT DOCUMENTS

2002/0095087 A1*  7/2002  Mourad et al. ............... 600/442
2005/0187471 A1    8/2005  Kanayama et al.
(Continued)

FOREIGN PATENT DOCUMENTS

CN    201207035 Y    3/2009
JP    2005-218684 A    8/2005
(Continued)

OTHER PUBLICATIONS

Kolkman et al. "In vivo photoacoustic imaging of blood vessels with a pulsed laser diode". Lasers Med Sci (2006) 21:134-139.*
(Continued)

*Primary Examiner* — Amanda Lauritzen Moher
*Assistant Examiner* — Shahdeep Mohammed
(74) *Attorney, Agent, or Firm* — Sughrue Mion, PLLC

(57) ABSTRACT

A photoacoustic imaging apparatus is equipped with an extracting section that extracts position data regarding the positions of each of a plurality of peaks in electrical signals that photoacoustic waves have been converted into, and positive/negative data that indicates whether the peaks are positive or negative. An image generating section administers chromatic adjustments to an image region corresponding to a signal region sandwiched between adjacent peaks based on the position data in the case that the positive/negative data for the adjacent peaks are in the order of positive then negative in temporal series, in order to facilitate discrimination of the pair of adjacent peaks and the signal region as being a single tissue system. Thereby, discrimination of a region between two lines is facilitated in photoacoustic imaging, even in cases that the boundary between a comparatively large tissue system and another tissue system is displayed as two lines.

20 Claims, 5 Drawing Sheets

(51) Int. Cl.
   *A61B 5/145*     (2006.01)
   *A61B 5/1455*    (2006.01)

(56) References Cited

U.S. PATENT DOCUMENTS

2011/0066023 A1    3/2011    Kanayama et al.
2011/0239766 A1   10/2011    Nakajima et al.

FOREIGN PATENT DOCUMENTS

| | | |
|---|---|---|
| JP | 2010-035806 A | 2/2010 |
| JP | 2010-069065 A | 4/2010 |
| JP | 2010-136887 A | 6/2010 |
| WO | 2010/067608 A1 | 6/2010 |
| WO | WO 2010/064249 A1 * | 6/2010 |

OTHER PUBLICATIONS

Communication dated Jul. 21, 2014, issued by the State Intellectual Property Office of the People's Republic of China in corresponding Application No. 201180052368.7.
International Search Report of PCT/JP2011/005843 dated Nov. 15, 2011 English Translation.

* cited by examiner

PHOTOACOUSTIC IMAGING APPARATUS AND METHOD FOR OPERATING A PHOTOACOUSTIC IMAGING APPARATUS

TECHNICAL FIELD

The present invention is related to a photoacoustic imaging apparatus that detects photoacoustic waves, which are generated within the body of a subject by light being irradiated on the subject, and generates photoacoustic images. The present invention is also related to a method for operating the photoacoustic imaging apparatus.

BACKGROUND ART

Ultrasound imaging, in which ultrasound images are generated by detecting ultrasonic waves which are reflected within the body of a subject by the ultrasonic waves being emitted within the body of the subject, to enable display of morphological tomographic images, is known as a conventional method for obtaining tomographic images of the interior of the body of a subject. Meanwhile, there have been recent advancements in the development of apparatuses which are capable of displaying not only morphological tomographic images but also functional tomographic images in examinations of subjects. One such apparatus is that which utilizes the photoacoustic analysis method. The photoacoustic analysis method emits light having a predetermined wavelength (visible light, near infrared light, or intermediate infrared light, for example) onto a subject, detects photoacoustic waves, which are elastic waves generated as a result of a specific substance within the subject absorbing the energy of the light, and quantitatively measures the concentration of the specific substance. The specific substance within the subject is glucose, hemoglobin, etc., which is included in blood. The technique that detects photoacoustic waves and generates photoacoustic images based on detected signals is referred to as PAI (Photo Acoustic Imaging) or PAT (Photo Acoustic Tomography).

Photoacoustic imaging images objects that have higher coefficients of light absorption than that of media that surround the objects. For example, the coefficient of light absorption of blood vessels within bodies is greater than that of the media that surrounds them, and imaging of blood vessels is being widely researched.

For example, it is known that photoacoustic waves which are generated from tissue systems having high coefficients of light absorption such as blood vessels are detected as N shaped acoustic signals as illustrated in FIG. 6A (Japanese Unexamined Patent Publication No. 2010-136887). Generally, the amount of time t between emission of light until detection of these acoustic signals is a value that reflects the position of the blood vessels with respect to a detector, and the width w of the acoustic signals is a value that reflects the size of the blood vessels. Coefficients of light absorption are calculated based on the photoacoustic waves described above, and photoacoustic images are obtained as a distribution of coefficients of light absorption.

DISCLOSURE OF THE INVENTION

No problems occur in the case that a positive peak P1 and a negative peak P2 of a photoacoustic wave are connected as illustrated in FIG. 6A. However, the distance between the position of a positive peak and the position of a negative peak becomes great for comparative large tissue systems such as thick blood vessels as illustrated in FIG. 6B. In such cases, only the boundaries thereof are displayed as two lines, and there is a problem that it is difficult for the two lines to be discriminated as a single tissue system. In some cases, such two lines may cause erroneous recognition that each of the two lines represents a comparatively small tissue system, such as two independent thin blood vessels. Further, in the case that there are a plurality of thick blood vessels, it is difficult to discriminate which lines are a pair of lines that represents a single tissue system, and the difficulty in discriminating individual tissue systems becomes conspicuous.

The present invention has been developed in view of the foregoing circumstances. It is an object of the present invention to provide a photoacoustic imaging apparatus that enables a region between two lines to be discriminated as a single tissue system in photoacoustic imaging that utilizes the photoacoustic effect, even in the case that the boundary between a comparatively large tissue system and another tissue system is displayed as the two lines. It is another object of the present invention to provide a method for operating the photoacoustic imaging apparatus.

A photoacoustic imaging apparatus of the present invention that achieves the above object comprises:
  a light emitting section that emits a measuring light beam into the body of a subject;
  an electroacoustic converting section that detects photoacoustic waves, which are generated within the body of the subject by the measuring light beam being irradiated thereon, and converts the photoacoustic waves into electrical signals;
  an image generating section that generates a photoacoustic image based on the electrical signals; and
  an extracting section that extracts position data regarding the positions of each of a plurality of peaks in the electrical signals that the photoacoustic waves have been converted into, and positive/negative data that indicates whether the peaks are positive or negative;
  the image generating section administering chromatic adjustments to an image region corresponding to a signal region sandwiched between a pair of adjacent peaks based on the position data of the peaks in the case that the positive/negative data for the pair of adjacent peaks from among the plurality of peaks are in the order of positive then negative in temporal series, as a correction process that facilitates discrimination of the pair of adjacent peaks and the signal region as being a single tissue system.

In the present specification, the "positive/negative data" of the peaks refers to information that represents whether the peaks have a positive intensity or a negative intensity with background as a reference. In the former case, the information indicates "positive", and in the latter case, the information indicates "negative", for example.

The "pair of adjacent peaks" refers to a combination of two peaks which are consecutively measured in temporal series from among the plurality of measured peaks.

That the "positive/negative data for the pair of adjacent peaks from among the plurality of peaks are in the order of positive then negative in temporal series" refers to a case in which the positive/negative data of a peak which is detected first within a pair of adjacent peaks is positive, and the positive/negative data of a peak which is detected next is negative. Here, the positive and negative signal peaks respectively refer to signals in cases that positive and negative pressure of acoustic waves are detected. In the case that the positive and negative pressures of acoustic waves are detected but the signal peaks become negative and positive due to the polarity of an amplifier, the signs in the following description will be reversed.

The "chromatic adjustment" means that at least one of the hue, luminosity (brightness), and saturation of the target image region is adjusted.

The photoacoustic imaging apparatus of the present invention may adopt a configuration, wherein:
the image generating section administers the chromatic adjustments such that the image region corresponding to the signal region sandwiched between the pair of adjacent peaks is emphasized and displayed.

The photoacoustic imaging apparatus of the present invention may adopt a configuration, wherein:
the image generating section administers chromatic adjustments to image regions corresponding to other tissue systems that did not undergo the correction process that enables the image region that underwent the correction process to be discriminated from the other tissue systems.

The "other tissue systems" refers to tissue systems different from the tissue system corresponding to the image region on which correction has been performed to facilitate discrimination as a single tissue system. The other tissue systems may be tissue systems of the same type, or tissue systems of other types.

It is preferable for the photoacoustic imaging apparatus of the present invention to adopt a configuration, wherein:
the image generating section performs the correction process only in a case in which the interval between the two adjacent peaks corresponds to a length of 5 mm or less when converted to a length within living tissue.

It is preferable for the photoacoustic imaging apparatus of the present invention to adopt a configuration, wherein:
the light emitting section is equipped with a light source unit that outputs the measuring light beam, which is capable of outputting light having different wavelengths as the measuring light beam; and
the image generating section performs the correction process by changing the format of chromatic adjustment for each wavelength of the measuring light beam.

It is preferable for the photoacoustic imaging apparatus of the present invention to further comprise:
a storage section that stores a first photoacoustic image generated by the image generating section; and for a configuration to be adopted, wherein:
the image generating section compares a first width of a first signal region that the chromatic adjustment was administered on within the first photoacoustic image, and a second width of a second signal region in which chromatic adjustment is to be administered when a second photoacoustic image is to be generated that corresponds to the first signal region, judges whether the rate of change from the first width to the second width is greater than or equal to a threshold value, and administers a predetermined chromatic adjustment to a second image region corresponding to the second signal region according to the result of judgment, in the case that a plurality of photoacoustic images are continuously imaged.

In the present specification, the "widths of signal regions" of the peaks refers to the distance between two adjacent peaks. The distance may be along a temporal axis, or along a displaced axis which is obtained by multiplying time by a predetermined speed of sound.

The "second signal region . . . that corresponds to the first signal region" refers to a second signal region having a relationship with the first signal region that the first signal region and the second signal region are signal regions that reflect photoacoustic waves generated by substantially the same tissue system.

It is preferable for the photoacoustic imaging apparatus of the present invention to adopt a configuration, wherein:
the extracting section extracts the position data and the positive/negative data from the electrical signals after matched addition is administered thereon.

A method for operating a photoacoustic imaging apparatus of the present invention is a method for operating a photoacoustic imaging apparatus that emits a measuring light beam into the body of a subject, detects photoacoustic waves, which are generated within the body of the subject by the measuring light beam being irradiated thereon, converts the photoacoustic waves into electrical signals, and generates a photoacoustic image based on the electrical signals, comprising:
extracting position data regarding the positions of each of a plurality of peaks in the electrical signals that the photoacoustic waves have been converted into, and positive/negative data that indicates whether the peaks are positive or negative; and
administering chromatic adjustments to an image region corresponding to a signal region sandwiched between a pair of adjacent peaks based on the position data of the peaks in the case that the positive/negative data for the pair of adjacent peaks from among the plurality of peaks are in the order of positive then negative in temporal series, as a correction process that facilitates discrimination of the pair of adjacent peaks and the signal region as being a single tissue system.

It is preferable for the method for operating a photoacoustic imaging apparatus of the present invention to adopt a configuration wherein:
the chromatic adjustments are administered such that the image region corresponding to the signal region sandwiched between the pair of adjacent peaks is emphasized and displayed.

The method for operating a photoacoustic imaging apparatus of the present invention may adopt a configuration wherein:
chromatic adjustments are administered to image regions corresponding to other tissue systems that did not undergo the correction process that enables the image region that underwent the correction process to be discriminated from the other tissue systems.

It is preferable for the method for operating a photoacoustic imaging apparatus of the present invention to adopt a configuration wherein:
the correction process is performed only in a case in which the interval between the two adjacent peaks corresponds to a length of 5 mm or less when converted to a length within living tissue.

It is preferable for the method for operating a photoacoustic imaging apparatus of the present invention to adopt a configuration wherein:
light beams having different wavelengths are output as the measuring light beam; and
the correction process is performed by changing the format of chromatic adjustment for each wavelength of the measuring light beam.

In the case that a plurality of photoacoustic images are continuously imaged, it is preferable for a configuration to be adopted, wherein:
a first generated photoacoustic image is stored; and
a first width of a first signal region that the chromatic adjustment was administered on within the first photoacoustic image is compared against a second width of a second signal region, in which chromatic adjustment is to be administered when a second photoacoustic image is to be generated, that corresponds to the first signal region;

judgment is rendered regarding whether the rate of change from the first width to the second width is greater than or equal to a threshold value; and a predetermined chromatic adjustment is administered to a second image region corresponding to the second signal region according to the result of judgment.

It is preferable for the method for operating a photoacoustic imaging apparatus of the present invention to adopt a configuration wherein:

the position data and the positive/negative data are extracted from the electrical signals after matched addition is administered thereon.

The photoacoustic imaging apparatus of the present invention and the method for operating the photoacoustic imaging apparatus of the present invention extract position data regarding the positions of each of a plurality of peaks in the electrical signals that the photoacoustic waves have been converted into, and positive/negative data that indicates whether the peaks are positive or negative; and administer chromatic adjustments to an image region corresponding to a signal region sandwiched between a pair of adjacent peaks based on the position data of the peaks in the case that the positive/negative data for the pair of adjacent peaks from among the plurality of peaks are in the order of positive then negative in temporal series, as a correction process that facilitates discrimination of the pair of adjacent peaks and the signal region as being a single tissue system. By this configuration, positive and negative peaks of photoacoustic waves can be handled as a pair even if the distance between the positions thereof are great, and an image that facilitate discrimination of the region between the peaks as continuously representing a single tissue system can be displayed. As a result, it becomes possible a region between two lines to be discriminated as a single tissue system in photoacoustic imaging that utilizes the photoacoustic effect, even in the case that the boundary between a comparatively large tissue system and another tissue system is displayed as the two lines.

BEST MODE FOR CARRYING OUT THE INVENTION

Figure 1:
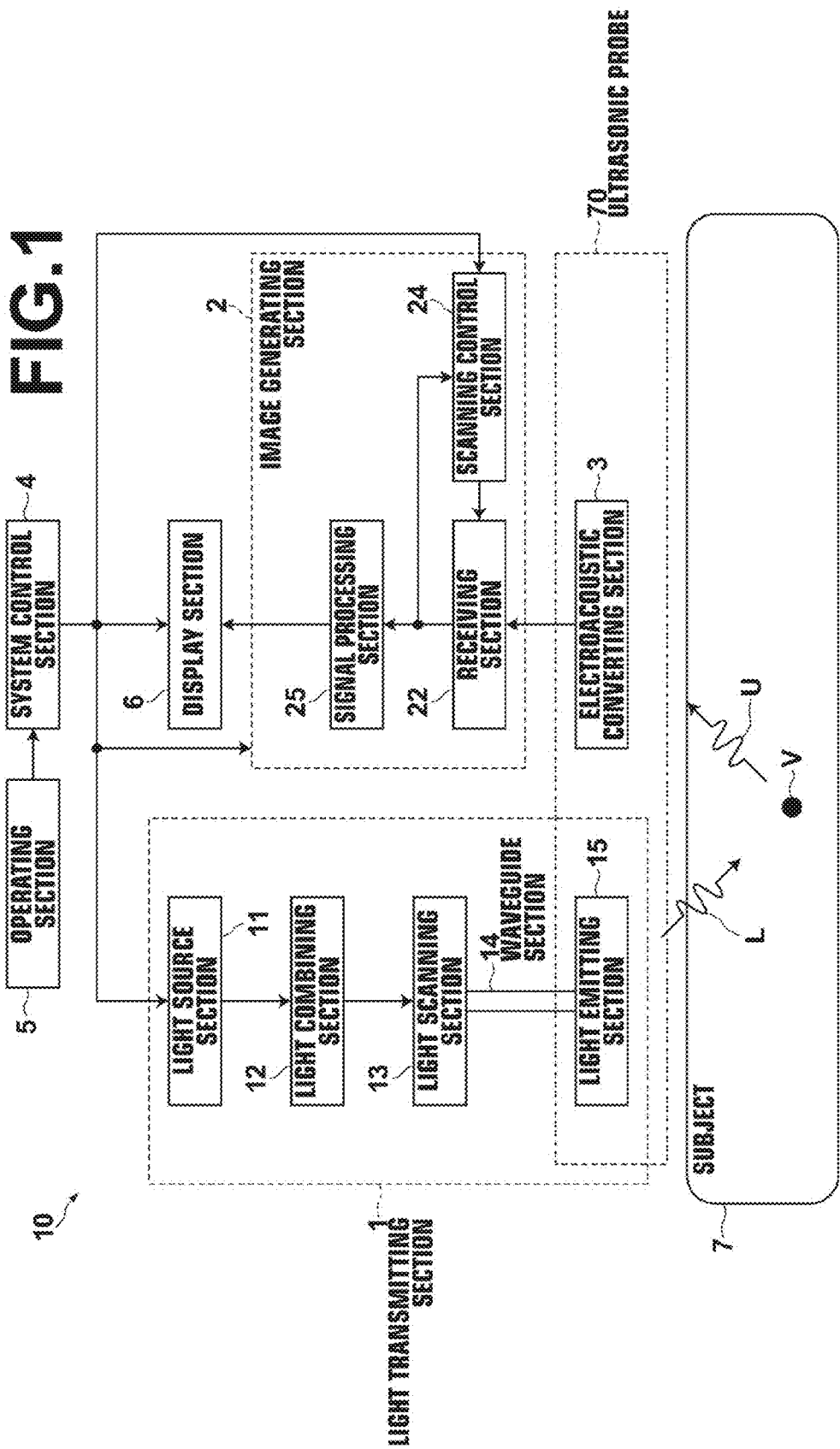
FIG. 1 is a schematic diagram that illustrates the configuration of a photoacoustic imaging apparatus according to an embodiment of the present invention.

Hereinafter, an embodiment of the present invention will be described with reference to the attached drawings. However, the present invention is not limited to the embodiment to be described below. Note that the dimensional ratios of the constituent elements in the drawings are different from the actual dimensional ratios in order to facilitate visual understanding.

Figure 2:
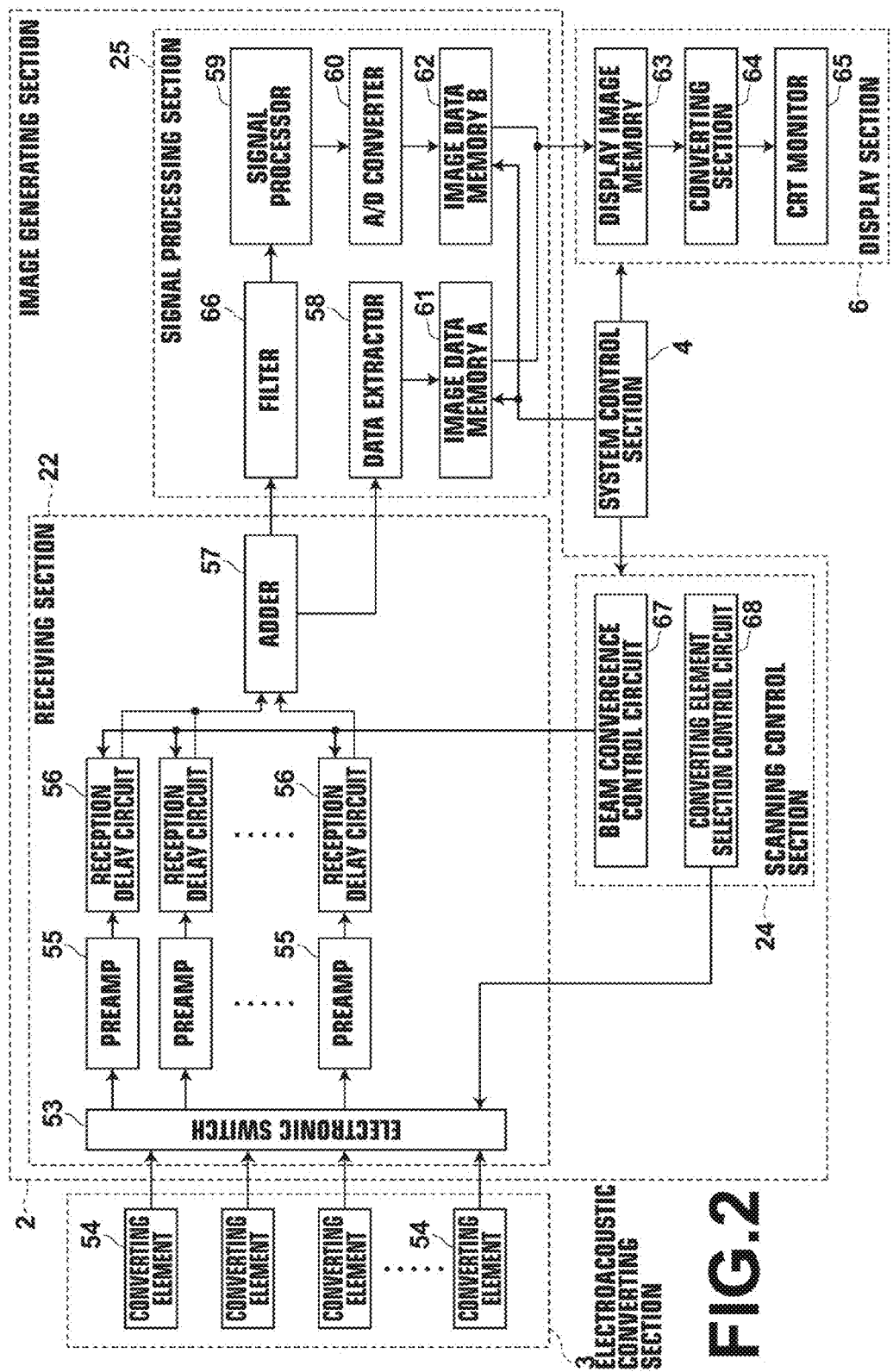
FIG. 2 is a schematic diagram that illustrates the configuration of an image generating section of FIG. 1.

A PAI (Photo Acoustic Imaging) apparatus 10 according to an embodiment of the present invention will be described. FIG. 1 is a block diagram that illustrates the schematic structure of the entirety of the PAI apparatus 10 of the present embodiment. FIG. 2 is a block diagram that illustrates the configuration of an image generating section 2 of FIG. 1.

The PAI apparatus 10 of the present embodiment is equipped with: a light transmitting section 1 that generates a measuring light beam L that includes a specific wavelength component and emits the measuring light beam L onto a subject 7; an image generating section 2 that detects photoacoustic waves U, which are generated within the body of the subject by the measuring light beam L being emitted onto the subject 7, and generates photoacoustic image data of a desired cross section; an electroacoustic converting section 3 that converts acoustic signals to electric signals; a display section 6 that displays the photoacoustic image data; an operating section 5 through which an operator inputs patient data and imaging conditions for the apparatus; and a system control section 4 that controls each component and the apparatus as a whole.

The light transmitting section 1 is equipped with: a light source section 11 having a plurality of light sources that output light beams having different wavelengths; a light combining section 12 that combines the light beams having a plurality of wavelengths into a single optical axis; a multiple channel waveguide section 14 that guides the light beams to the body surface of the subject 7; a light scanning section 13 that switches the channel of the waveguide section 14 to be utilized and performs scanning; and a light emitting section 15 that outputs the light beams provided by the waveguide section 14 toward the subject 7.

The light source section 11 has one or more light sources that emit light beams having predetermined wavelengths. Light emitting elements such as semiconductor lasers (LD's), light emitting diodes (LED's), solid state lasers, gas lasers, etc. that emit specific wavelength components or single color light beams that include the specific wavelength components may be employed as the light sources. It is preferable for a light source 16 to output pulsed light having a pulse width within a range from 1 nsec to 100 nsec as the measuring light beam. The wavelength of the measuring light beam is determined as appropriate according to the light absorbing properties of the substance within the subject's body which is the target of measurement. The optical absorption properties of hemoglobin differ according to the state thereof (oxidized hemoglobin, reduced hemoglobin, methemoglobin, carbon gas hemoglobin, etc.), but hemoglobin generally absorbs light having wavelengths from 600 nm to 1000 nm. Accordingly, in the case that the measurement target is hemoglobin within an organism (that is, a case in which blood vessels are imaged), it is generally preferable for the wavelength of the measuring light beam to be within a range from 600 nm to approximately 1000 nm. It is further preferable for the wavelength of the measuring light beam to be within a range from 700 nm to 1000 nm, from the viewpoint of being able to reach deep portions of a subject M. The output of the measuring light beam is preferably within a range from 10 μJ/cm$^2$ to several tens of μJ/cm$^2$ from the viewpoint of transmission loss of light and photoacoustic waves, photoacoustic conversion efficiency, detection sensitivity of presently available detectors, etc. It is further preferable for repetition of the pulsed light output to be 10 Hz or greater from the viewpoint of image construction speed. In addition, the measuring light beam may be a pulse row, in which a plurality of the pulsed light beams are arranged. The light beams having different wavelengths may be simultaneously irradiated onto the subject 7, or may be irradiated onto the subject 7 at temporally separated timings.

As a more specific example, a Nd:YAG laser (light emission wavelength: 1064 nm), which is a type of solid state laser, or a He—Ne gas laser (light emission wavelength: 633 nm), which is a type of gas laser, may be employed to form a laser light beam having a pulse width of approximately 10 nsec in the case that the concentration of hemoglobin in the subject 7 is to be measured. In the case that a miniature light emitting element such as a LD or a LED is employed, an element that employs materials such as InGaAlP (light emission wavelength: 550 nm to 650 nm), GaAlAs (light emission wavelength: 650 nm to 900 nm), and InGaAs or InGaAsP (light emission wavelength: 900 nm to 2300 nm) may be utilized. In addition, light emitting elements that employ InGaN and emit light having wavelengths of 550 nm or less are recently being put into practical use. Further, an OPO (Optical Parametrical Oscillator) laser that employs a non linear optical crystal to enable wavelengths to be varied may be employed.

The light combining section 12 causes light beams having different wavelengths emitted by the light source section 11 to be overlapped along a single optical axis. Each light beam is converted to a collimated light beam by a collimating lens, then the optical axis thereof is matched by a perpendicular prism or a dichroic prism. A comparatively small combining optical system can be constituted by such a configuration. Alternatively, commercially available multiplex wavelength combiner/separators may be employed. In the case that a light source capable of continuously changing wavelengths such as the aforementioned OPO laser is utilized in the light source section 11, the light combining section 12 is not necessary.

The waveguide section 14 guides the measuring light beam output by the light combining section 12 to the light emitting section 15. Optical fibers or thin film optical waveguides are employed in order to perform efficient light propagation. Alternatively, direct spatial propagation is also possible. Here, the waveguide section 14 is constituted by a plurality of optical fibers 71. A specific optical fiber 71 is selected from among the plurality of optical fibers 71, and light is irradiated onto the subject 7 by the selected optical fiber 71. Note that although not clearly illustrated in FIG. 1, the optical fibers may be utilized in combination with optical systems such as optical filters and lenses.

The light scanning section 13 scans the subject 7 with the measuring light beam, by sequentially selecting optical fibers from among the plurality of optical fibers 71 which are arranged in the waveguide section 14 and emitting the measuring light beam.

In the present embodiment, the light emitting section 15 is constituted by a plurality of output end portions of the plurality of optical fibers 71. The light emitting section 15 and the electroacoustic converting section 3 constitute an ultrasonic probe 70. The plurality of output end portions of the plurality of optical fibers 71 are arranged along the periphery of the electroacoustic converting section 3. In the case that a plurality of converting elements 54 that constitute the electroacoustic converting section 3 are formed by a transparent material, the light emitting section 15 may be provided to irradiate the entirety of the converting elements from above the converting elements 54. Note that the plurality of output end portions of the plurality of optical fibers 71 form a flat surface, a convex surface, or a concave surface along with the plurality of converting elements 54 that constitute the electroacoustic converting section 3. Here, a case will be described in which the surface formed by the plurality of output portions and the converting elements 54 is a flat surface.

The electroacoustic converting section 3 is constituted by a plurality of very fine converting elements 54 which are arranged either one dimensionally or two dimensionally. The converting elements 54 are piezoelectric elements formed by a piezoelectric ceramic or a polymer film such as PVDF (polyvinylidene fluoride). The electroacoustic converting section 3 receives photoacoustic waves U which are generated within the subject 7 by the light emitting section 15 emitting the measuring light beam L thereon. The converting elements 54 function to convert the received photoacoustic waves U into electrical signals. The electroacoustic converting section 3 is configured to be small and lightweight, and is connected to a receiving section 22 to be described later by a multiple channel cable. The electroacoustic converting section 3 is selected from a sector scanning type, a linear scanning type, and a convex scanning type according to body parts to be diagnosed. The electroacoustic converting section 3 may be equipped with an acoustic rectifying layer in order to efficiently transmit the photoacoustic waves U. Generally, the acoustic impedances of piezoelectric materials and living tissue greatly differ. Therefore, in cases that a piezoelectric material directly contacts living tissue, reflection at the interface thereof becomes great, and photoacoustic waves cannot be efficiently transmitted. However, photoacoustic waves can be efficiently transmitted by inserting an acoustic rectifying layer formed by a substance having an intermediate acoustic impedance between the piezoelectric material and the living tissue. Examples of materials of the acoustic rectifying layer include epoxy resin and quartz glass.

The image generating section 2 of the PAI apparatus 10 is equipped with: a receiving section 22 that selectively drives the plurality of converting elements 54 that constitute the electroacoustic converting section 3, imparts predetermined delays to electrical signals output by the electroacoustic converting section 3, and generates received signals by performing phase matched addition; a scanning control section 24 that controls the selective driving of the converting elements 54 and the delay time imparted by the receiving section 22; and a signal processing section 25 that administers various processes on the received signals obtained from the receiving section 22.

As illustrated in FIG. 2, the receiving section 22 is equipped with an electronic switch 53, preamps 55, reception delay circuits 56, and an adder 57.

The electronic switch 53 continuously selects a predetermined number of adjacent converting elements 54 when receiving photoacoustic waves during photoacoustic scanning. For example, in the case that the electroacoustic converting section 3 is constituted by 192 converting elements CH1 through CH192 in an array, the arrayed converting elements are divided into three regions, which are: Area 0 (a region from converting element CH1 through converting element 64); Area 1 (a region from converting element CH65 through converting element 128); and Area 2 (a region from converting element CH129 through converting element 192). The arrayed converting elements constituted by N converting elements are handled as groups (areas) of n (n<N) adjacent converting elements in this manner. In the case that imaging operations are executed for each area, the need to connect preamps and A/D converting boards to converting elements for each channel is obviated, thereby simplifying the configuration of the ultrasonic probe 70 and preventing cost increases. In addition, in the case that a plurality of optical fibers are provided such that light can be emitted individually onto each area, the light output for each emission can be kept low. Therefore, an advantage is obtained, that the need to employ a costly high output light source is obviated. The electrical signals obtained by each of the converting elements 54 are provided to the preamps 55.

The preamps 55 amplify the weak electrical signals received from the selected converting elements 54, to secure a sufficient S/N ratio.

The reception delay circuit 56 imparts a delay time to the electrical signals corresponding to the photoacoustic waves U obtained from the converting elements 54 selected by the electronic switch 53, in order to form a convergent received beam in which the phases of the photoacoustic waves U from a predetermined direction are matched.

The adder 57 adds the electrical signals output from the plurality of channels and delayed by the reception delay circuit 56 to organize the electrical signals into a single received signal. The addition adds acoustic signals from a predetermined depth by phase matched addition, and sets a reception convergence point (ST1 through ST3 of FIG. 3).

The scanning control section 24 is equipped with: a beam convergence control circuit 67 and a converting element selection control circuit 68. The converting element selection control circuit 68 provides position data of the predetermined number of converting elements 54, to be selected by the electronic switch 53 during signal reception, to the electronic switch 53. Meanwhile, the beam convergence control circuit 67 provides delay time information for the predetermined number of converting elements 54 to form the reception convergence point to the reception delay circuit 56.

Figure 3:
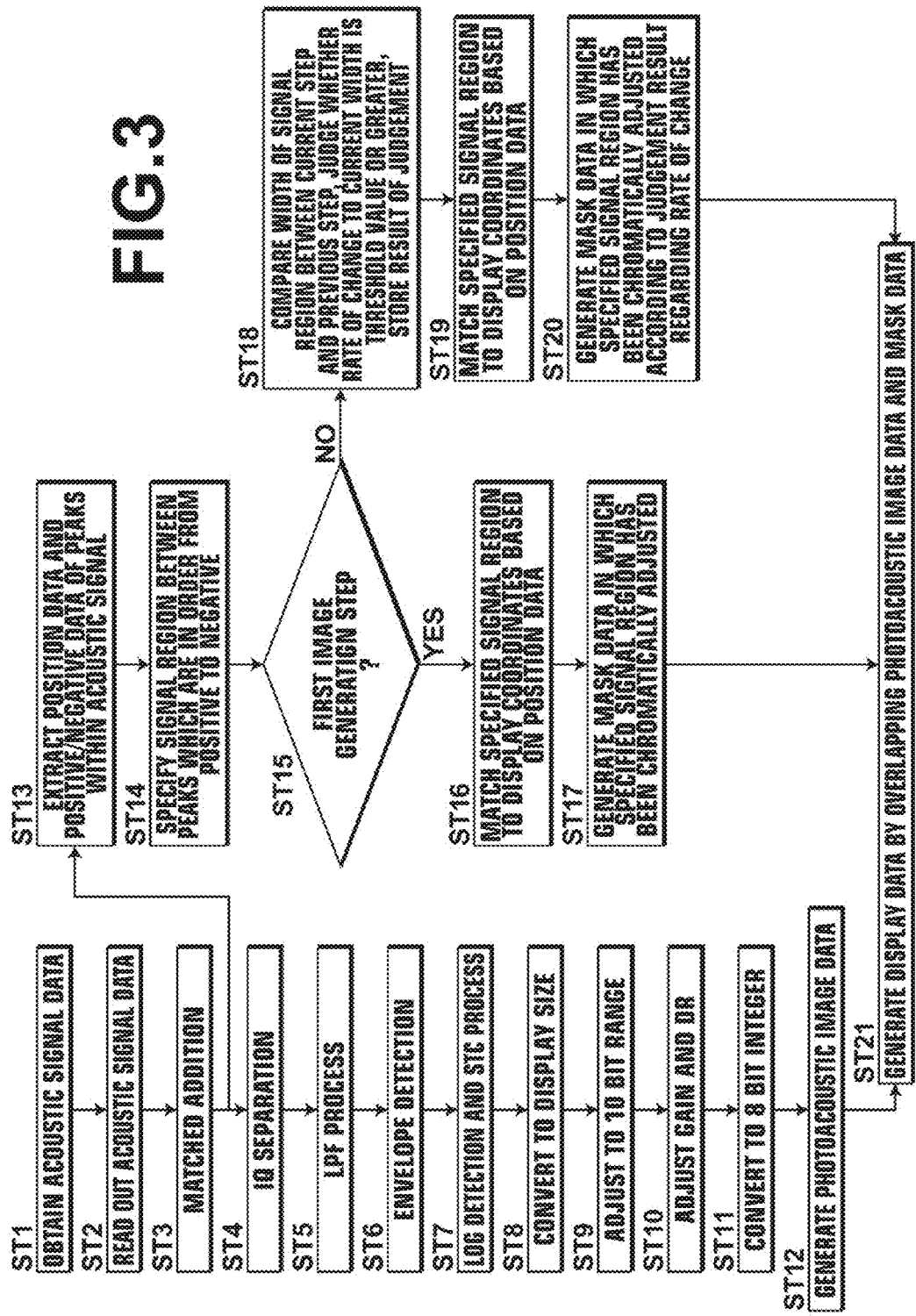
FIG. 3 is a block diagram for explaining an image generating process performed by the embodiment of the present invention.

The signal processing section 25 is equipped with: a filter 66; a data extractor 58; a signal processor 59; an A/D converter 60; an image data memory A 61; and an image data memory B 62. In the present invention, the signal processing section 25 extracts position data regarding the positions of each of a plurality of peaks in the electrical signals that the photoacoustic waves have been converted into, and positive/negative data that indicates whether the peaks are positive or negative. In the case that a pair of adjacent peaks from among the plurality of peaks are in the order of positive then negative in temporal series, the signal processing section 25 administers chromatic adjustments to an image region corresponding to a signal region sandwiched between the pair of adjacent peaks based on the position data of the peaks, as a correction process that facilitates discrimination of the pair of adjacent peaks and the signal region as being a single tissue system. Specifically, the following signal processes are performed as illustrated in FIG. 3.

First, acoustic signal data, which are the electrical signals output from the adder 57 of the receiving section 22, are processed by the filter 66 of the signal processing section 25 such that unnecessary noise is removed therefrom by IQ separation (ST4) and a LPF process (ST5). Thereafter, the signal processor 59 administers processes such as envelope detection (ST6), logarithmic detection and a STC process (ST7), conversion to a display size (ST8), adjustment to a 10 bit range (ST9), gain and DR adjustments (ST10), and conversion to 8 bit integers (ST11). The A/D converter 60 administers A/D conversion to the signals output by the signal processor 59.

The image data memory B 62 is a memory circuit that stores the acoustic signal data which have undergone A/D conversion. Under control of the system control section 4, data regarding cross sections are read out from the image data memory B 62, and photoacoustic image data of the cross sections are generated by spatial interpolation during the readout (ST12).

The data extractor 58 extracts position data regarding the positions of each of a plurality of peaks in the photoacoustic signal data output by the adder 57 of the receiving section 22, and positive/negative data that indicates whether the peaks are positive or negative (ST13). In the present embodiment, the data extractor 58 corresponds to the extracting section of the present invention. The position data of the peaks is not particularly limited as long as it is information that enables the positions of the peaks to be specified. In the case that the acoustic signal data are represented along a temporal axis, for example, the position data may be specific times along the temporal axis. The data extractor 58 detects pairs of peaks which are in the order of positive then negative in temporal series. If such a pair of peaks is present, a signal region sandwiched between such adjacent peaks is specified (ST14). The ends of the signal region sandwiched by such a pair of peaks are selected from positions at which the values of the peaks are maximal and positions at which the values are half maximum full width, for example. Thereafter, in the case that the image generating step is a first image generating step (ST15), a process is performed to match the specified signal region to coordinates of a display size, based on the position data of the pair of adjacent peaks (ST16). Next, chromatic adjustment is administered onto an image region corresponding to the specified signal region, to generate mask data for a correction process that facilitates the two adjacent peaks and the signal region as a single tissue system (ST17). The mask data is stored in the image data memory A 61.

Note that in the present embodiment, it is preferable for the image generating section to perform the correction process only in a case in which the interval between the two adjacent peaks corresponds to a length of 5 mm or less when converted to a length within living tissue. That is, the present embodiment generates the mask data only in the case that the interval between the two adjacent peaks corresponds to a length of 5 mm or less when converted to a length within living tissue. Judgment regarding whether the interval between the two adjacent peaks corresponds to a length of 5 mm or less when converted to a length within living tissue is rendered based on the position data regarding each peak. That the "the interval between the two adjacent peaks corresponds to a length of 5 mm or less when converted to a length within living tissue" means that the width of the signal region sandwiched between two adjacent peaks, which is obtained based on the difference in the position data of each of the two peaks, is 5 mm or less when converted to a distance along a spatial displaced axis. For example, in the case that the position data of two adjacent peaks are specific times along a temporal axis, the temporal difference obtained from the difference in times and the speed of sound within living tissue are employed to calculate a distance corresponding to the width of the signal region sandwiched between the two peaks. Note that if the speed of sound within living tissue is designated as 1530 m/sec, for example, the temporal difference along a temporal axis that corresponds to a length of 5 mm within living tissue is 3268 μsec.

Generally, tissue systems that exceed 5 mm are also capable of being discriminated within ultrasound images obtained by ultrasonic imaging. Accordingly, there are cases in which it is sufficient to image only tissue systems which are 5 mm or less and cannot be discriminated within ultrasound images. In such cases, the amount of calculation time required for data processing can be reduced, and images can be expediently displayed, by performing correction to facilitate discrimination of tissue systems which are 5 mm or less as a single tissue system.

With respect to peaks which are not specified as pairs of adjacent peaks which are in the order of positive then negative in temporal series, the data extractor may not execute any particular chromatic adjustments, or may execute chromatic adjustment that warns that the peaks are not normal.

The mask data for performing chromatic adjustment to the image region is data for executing a mask process for administering a correction process that facilitates discrimination of the two adjacent peaks which are in the order of positive then negative in temporal series and the signal region sandwiched between the two peaks as being a single tissue system. The mask data is not particularly limited as long as it enables discrimination of the two adjacent peaks and the signal region sandwiched between the two peaks as being a single tissue system to be facilitated. Examples of mask data include: that which fills the image region between the two peaks with a color of the same series as the color displayed at the positions of each of the peaks; and that which fills the image region between the two peaks with an emphasizing color other than the color displayed at the positions of the peaks. Commonly, photoacoustic waves become attenuated the longer the propagation distance thereof becomes. Accordingly, the intensity of the peak which is detected later from between the two adjacent peaks will be less than the intensity of the peak which is detected first. When filling in the image region between the peaks, the luminosity of region may be adjusted to change continuously from a luminosity corresponding to the intensity of the first detected peak and a luminosity corresponding to the intensity of the later detected peak.

In photoacoustic imaging, there are cases in which image portions are displayed with emphasis not for the purpose of facilitating discrimination of individual tissue systems, but for the purpose of facilitating viewing. In such cases, it is preferable for chromatic adjustments to be executed on image regions corresponding to other tissue systems that did not undergo the correction process, that enables the image region that underwent the correction process to be discriminated from the other tissue systems. Thereby, whether a tissue system has undergone the correction process can be judged easily.

In addition, in the case that a light source unit that outputs the measuring light beam to the light emitting section is capable of outputting light beams having different wavelengths as the measuring light beam L, it is preferable for the correction process to be administered by changing the format of chromatic adjustment for each wavelength of the measuring light beam. Emission of the measuring light beam is performed at different times. The image generating section 2 (the data extractor 58, for example, in the present embodiment) obtains wavelength information regarding the emitted measuring light beam via the system control section 4, and mask data is generated according to the wavelength information. By adopting this configuration, discrimination of tissue systems having different light absorbing properties can be facilitated. The tissue systems having different light absorbing properties are not limited to different types of tissue systems, but also include tissue systems of the same type, of which the light absorbing properties change according to the states thereof, such as arteries and veins.

Meanwhile, in the present embodiment, in the case that the image generating step is a second or subsequent image generating step at ST15 (FIG. 3), the data extractor 58 compares the width of signal regions between two peaks of the current image generating step and the width of the signal region between two peaks corresponding to the two peaks of a previous image generating step, and judges whether the rate of change in the widths is greater than or equal to a threshold value (ST18). The result of the judgment is also stored in the image data memory A 61. Then, a process is performed to match a specified signal region to coordinates of a display size, based on the position data of the pair of adjacent peaks (ST19). Next, mask data that chromatically adjusts the specified signal region according to the result of judgment is generated (ST20). This mask data is stored in the image data memory A 61. By executing chromatic adjustment in this manner, chromatic adjustment can be performed according to the degree of expansion and contraction of a blood vessel, in the case that that the tissue system is a blood vessel. For example, if the rate of change in the interval between two adjacent peaks is comparatively large, it is considered that the signal region sandwiched between the peaks are photoacoustic waves generated by arteries, and if the rate of change is comparatively small, it is considered that the signal region sandwiched between the peaks are photoacoustic waves generated by veins. Accordingly, as the chromatic adjustment, mask data that emphasizes the image region corresponding to the signal region in red may be generated in the case that the rate of change is greater than or equal to the threshold value (30%, for example), and mask data that emphasizes the image region in blue may be generated in the case that the rate of change is less than the threshold value. The threshold value is set as appropriate, taking the rates of expansion and contraction of arteries and veins into consideration. Note that the previous image generating step need not necessarily be an image generating step which was executed immediately prior to the current image generating step.

The display section 6 is equipped with: a display image memory 63; a photoacoustic image data converter 64; and a monitor 65. The display image memory 63 is a buffer memory that temporarily stores photoacoustic image data and mask data which are to be displayed on the monitor 65. The photoacoustic image data from the image data memory B 62 and the mask data from the image data memory A 61 are overlapped in the display image memory 63 and combined into a single frame. Photoacoustic image data in which chromatic adjustment is executed is obtained by overlapping the photoacoustic image data and the mask data in this manner. The photoacoustic image data converter 64 performs D/A conversion and television format conversion on the combined image data read out from the display image memory 63. The output of the photoacoustic image data converter 64 is displayed by the monitor 65.

Note that in the description above, the data extractor 58 extracts the position data and the positive/negative data from the acoustic signal data output by the adder 57. However, the present invention is not limited to such a configuration, and the position data of the peaks may be extracted from acoustic signal data after envelope detection is performed, for example. In such a case, the actual peak positions of acoustic signal data can be extracted without being influenced by a resonant frequency of a converting element if a piezoelectric ceramic having a narrow receivable ultrasonic frequency band such as PZT is employed, by extracting the peaks of the envelope curve. Further, another advantageous effect is obtained, that the actual positive/negative state of acoustic signal data can be extracted, by extracting the positive/negative data of a first peak from acoustic signal data which are resonating in each envelope curve. In addition, the acoustic signal data is not limited to that which has undergone matched addition. Data, on which a signal process that employs Fourier transform, may be utilized.

The operating section 5 is equipped with a keyboard, a trackball, a mouse, etc. on an operating panel, and is employed by an operator to input necessary information, such as patient data, imaging conditions, and cross sections to be displayed.

The system control section 4 is equipped with a CPU (not shown) and a memory circuit (not shown). The system control section 4 controls each of the components, such as the light transmitting section 1, the image generating section 2, the display section 6, and the system as a whole, according to command signals input via the operating section 5.

Figure 4:
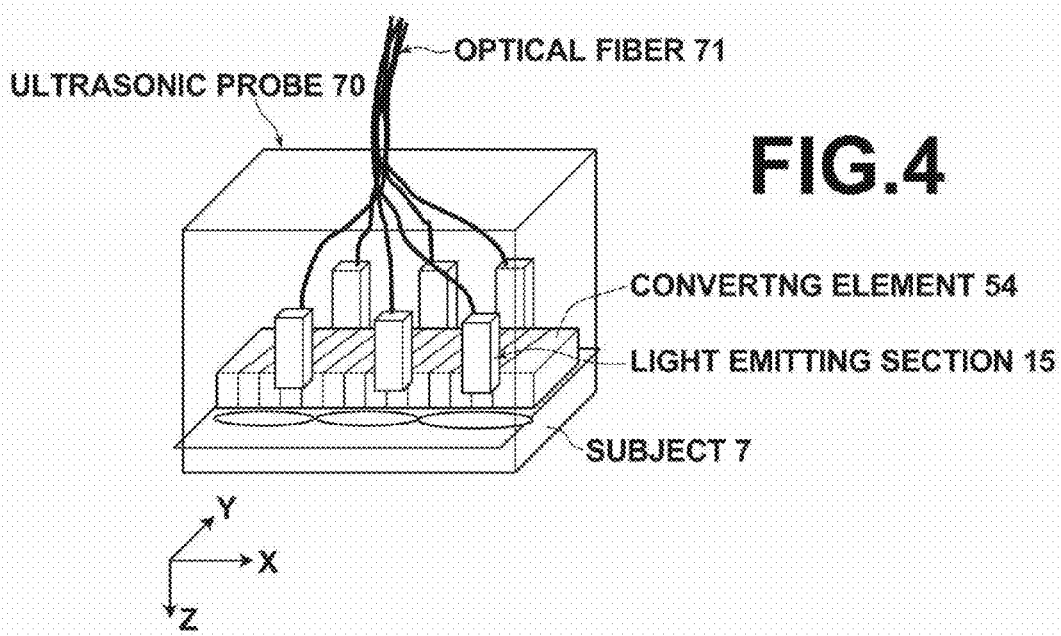
FIG. 4 is a schematic perspective view that illustrates an ultrasonic probe of the embodiment of the present invention.
Figure 5:
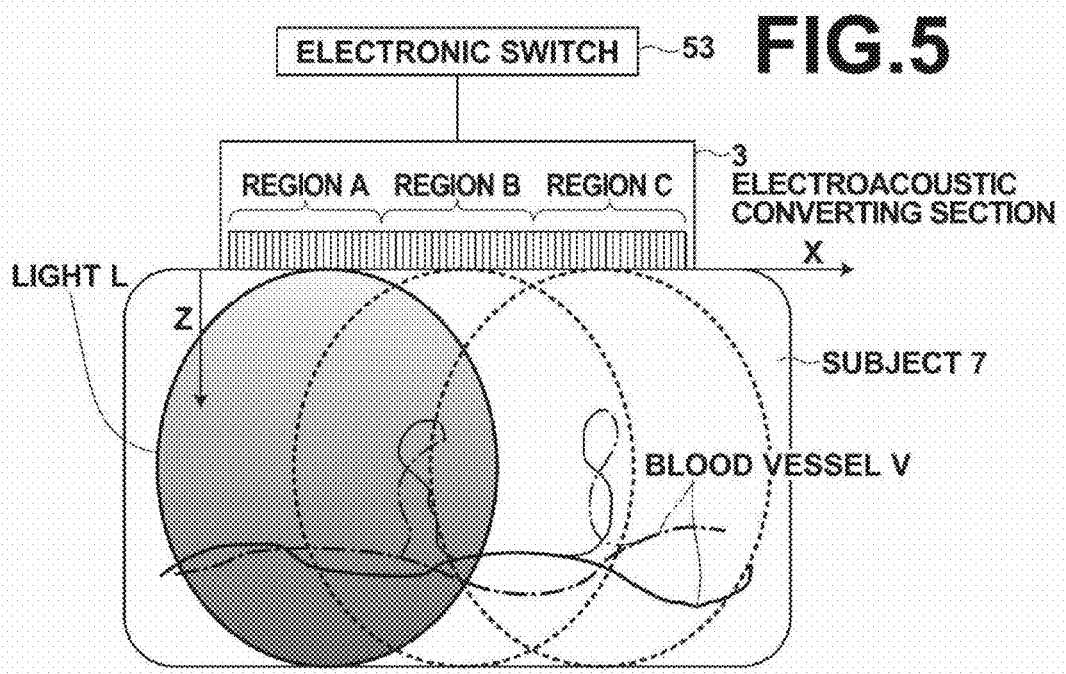
FIG. 5 is a schematic sectional diagram that illustrates the ultrasonic probe and living tissue when generating a photoacoustic image.
Figure 6A:
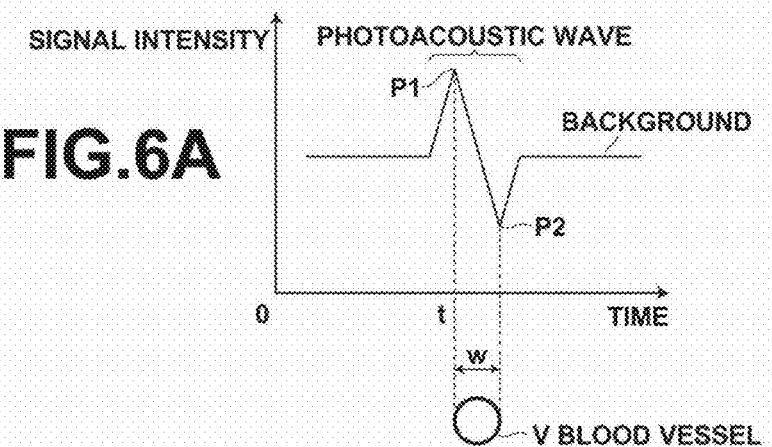
FIG. 6A is a schematic diagram fro explaining the shape of a photoacoustic wave generated by a small subject (absorber).
Figure 6B:
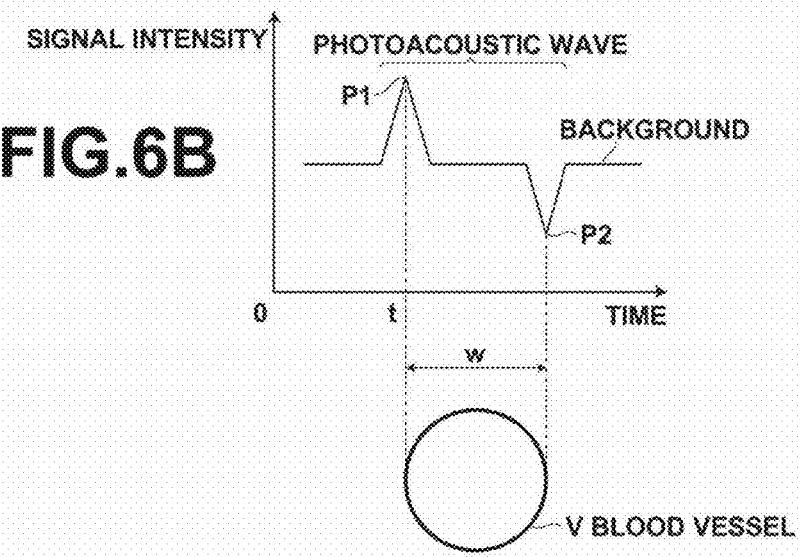
FIG. 6B is a schematic diagram fro explaining the shape of a photoacoustic wave generated by a large subject (absorber).

Next, the ultrasonic probe 70, in which the light emitting section 15 and the electroacoustic converting section 3 are integrated, will be described with reference to FIG. 4 and FIG. 5. FIG. 4 is a schematic diagram that illustrates the configuration of the ultrasonic probe 70. FIG. 5 illustrates the ultrasonic probe 70 and living tissue when generating a photoacoustic image.

The ultrasonic probe 70 has the plurality of converting elements 54. The converting elements 54 are arranged one dimensionally along a predetermined direction, for example. The optical fibers 71 guide light from the light source section 11 (FIG. 1) to the light emitting section 15 provided within the ultrasonic probe 70. The light emitting section 15 may be configured to emit the measuring light beam output by the light source section 11 onto a region that includes a selected partial region at least. For example, the light emitting section 15 is provided corresponding to each of a region A, a region B, and a region C. In this case, the light emitting section 15 corresponding to the region A emits the measuring light beam at least onto the region A when the region A is selected. The light emitting section 15 corresponding to the region B emits the measuring light beam at least onto the region B when the region B is selected. The light emitting section 15 corresponding to the region C emits the measuring light beam at least onto the region C when the region C is selected.

The ultrasonic probe 70 has converting elements 54 corresponding to 192 channels, for example. Consider a case in which the width corresponding to the converting elements 54 is divided into three partial regions (regions A through C) related to photoacoustic image generation, and the width of each partial region corresponds to converting elements 54 for 64 channels, for example. In this case, if the width of living tissue corresponding to 192 channels is 57.6 mm, the width of each partial region will be 19.2 mm. That is, the photoacoustic imaging apparatus 10 repeats light emission and data collection to and from 19.2 mm wide partial regions divided as illustrated in FIG. 5 three times, to obtain data for all 192 channels.

Hereinafter, the operative effects of the present invention will be described.

As described above, the photoacoustic imaging apparatus of the present invention and the method for operating the photoacoustic imaging apparatus of the present invention extract position data regarding the positions of each of a plurality of peaks in the electrical signals that the photoacoustic waves have been converted into, and positive/negative data that indicates whether the peaks are positive or negative; and administer chromatic adjustments to an image region corresponding to a signal region sandwiched between a pair of adjacent peaks based on the position data of the peaks in the case that the positive/negative data for the pair of adjacent peaks from among the plurality of peaks are in the order of positive then negative in temporal series, as a correction process that facilitates discrimination of the pair of adjacent peaks and the signal region as being a single tissue system. By this configuration, positive and negative peaks of photoacoustic waves can be handled as a pair even if the distance between the positions thereof are great, and an image that facilitate discrimination of the region between the peaks as continuously representing a single tissue system can be displayed. This is because the fact that generally, when photoacoustic waves related to healthy tissue are detected, a positive peak is observed first and then a negative peak is observed, is utilized. As a result, it becomes possible a region between two lines to be discriminated as a single tissue system in photoacoustic imaging that utilizes the photoacoustic effect, even in the case that the boundary between a comparatively large tissue system and another tissue system is displayed as the two lines.

Further, in the case that a plurality of photoacoustic images are imaged continuously, if a first generated photoacoustic image is stored; a first width of a first signal region that the chromatic adjustment was administered on within the first photoacoustic image is compared against a second width of a second signal region, in which chromatic adjustment is to be administered when a second photoacoustic image is to be generated, that corresponds to the first signal region; judgment is rendered regarding whether the rate of change from the first width to the second width is greater than or equal to a threshold value; and a predetermined chromatic adjustment is administered to a second image region corresponding to the second signal region according to the result of judgment; chromatic adjustment can be executed according to the degree of expansion and contraction of tissue systems.

What is claimed is:

1. A photoacoustic imaging device, comprising:
   an ultrasonic probe including:
      a light emitter that emits a measuring light beam into the body of a subject; and
      an electroacoustic convertor that detects photoacoustic waves, which are generated within the body of the subject by the measuring light beam being irradiated thereon, and converts the photoacoustic waves into electrical signals; and
   a processor which operates as:
      an image generator that generates a photoacoustic image based on the electrical signals; and
      an extractor that extracts position data regarding the positions of each of a plurality of peaks in the electrical signals that the photoacoustic waves have been converted into, and positive/negative data that indicates whether the peaks are positive or negative, and detects a signal region sandwiched between a pair of adjacent peaks based on the position data of the peaks in the case that the positive/negative data for the pair of adjacent peaks from among the plurality of peaks are in the order of positive then negative in temporal series;

wherein the image generator administers chromatic adjustments to an image region corresponding to the signal region if (i) the signal region includes a flat zone in which signal intensity is constant; and (ii) the positive peak, the flat zone, and the negative peak are detected in this order in temporal series, as a correction process that facilitates discrimination of the pair of adjacent peaks and the signal region as being a single tissue system, and wherein the chromatic adjustments include generating mask data which are data for executing a mask process for administering the correction process and overlapping the photoacoustic image and the mask data.

2. A photoacoustic imaging apparatus as defined in claim 1, wherein:

the light emitter is equipped with a light source that outputs the measuring light beam, which is capable of outputting light having different wavelengths as the measuring light beam; and the image generator performs the correction process by changing the format of chromatic adjustment for each wavelength of the measuring light beam.

3. A photoacoustic imaging apparatus as defined in claim 1, further comprising:

a storage that stores a first photoacoustic image generated by the image generator, and wherein:

the image generator compares a first width of a first signal region that the chromatic adjustment was administered on within the first photoacoustic image, and a second width of a second signal region in which chromatic adjustment is to be administered when a second photoacoustic image is to be generated that corresponds to the first signal region, judges whether the rate of change from the first width to the second width is greater than or equal to a threshold value, and administers a predetermined chromatic adjustment to a second image region corresponding to the second signal region according to the result of judgment, in the case that a plurality of photoacoustic images are continuously imaged.

4. A photoacoustic imaging apparatus as defined in claim 1, wherein:

the extractor extracts the position data and the positive/negative data from the electrical signals after matched addition is administered thereon.

5. A photoacoustic imaging apparatus as defined in claim 1, wherein:

the image generator administers the chromatic adjustments such that the image region corresponding to the signal region sandwiched between the pair of adjacent peaks is emphasized and displayed.

6. A photoacoustic imaging apparatus as defined in claim 5, further comprising:

a storage that stores a first photoacoustic image generated by the image generating section; and wherein:

the image generator compares a first width of a first signal region that the chromatic adjustment was administered on within the first photoacoustic image, and a second width of a second signal region in which chromatic adjustment is to be administered when a second photoacoustic image is to be generated that corresponds to the first signal region, judges whether the rate of change from the first width to the second width is greater than or equal to a threshold value, and administers a predetermined chromatic adjustment to a second image region corresponding to the second signal region according to the result of judgment, in the case that a plurality of photoacoustic images are continuously imaged.

7. A photoacoustic imaging apparatus as defined in claim 1, wherein:

the image generator administers chromatic adjustments to image regions corresponding to other tissue systems that did not undergo the correction process that enables the image region that underwent the correction process to be discriminated from the other tissue systems.

8. A photoacoustic imaging apparatus as defined in claim 7, further comprising:

a storage that stores a first photoacoustic image generated by the image generator; and wherein:

the image generator compares a first width of a first signal region that the chromatic adjustment was administered on within the first photoacoustic image, and a second width of a second signal region in which chromatic adjustment is to be administered when a second photoacoustic image is to be generated that corresponds to the first signal region, judges whether the rate of change from the first width to the second width is greater than or equal to a threshold value, and administers a predetermined chromatic adjustment to a second image region corresponding to the second signal region according to the result of judgment, in the case that a plurality of photoacoustic images are continuously imaged.

9. A photoacoustic imaging apparatus as defined in claim 1, wherein:

the image generator performs the correction process only in a case in which the interval between the two adjacent peaks corresponds to a length of 5 mm or less when converted to a length within living tissue.

10. A photoacoustic imaging apparatus as defined in claim 9, further comprising:

a storage that stores a first photoacoustic image generated by the image generator; and wherein:

the image generator compares a first width of a first signal region that the chromatic adjustment was administered on within the first photoacoustic image, and a second width of a second signal region in which chromatic adjustment is to be administered when a second photoacoustic image is to be generated that corresponds to the first signal region, judges whether the rate of change from the first width to the second width is greater than or equal to a threshold value, and administers a predetermined chromatic adjustment to a second image region corresponding to the second signal region according to the result of judgment, in the case that a plurality of photoacoustic images are continuously imaged.

11. A photoacoustic imaging method, comprising:

emitting a measuring light beam into the body of a subject;

detecting photoacoustic waves, which are generated within the body of the subject by the measuring light beam being irradiated thereon;

converting the photoacoustic waves into electrical signals;

generating a photoacoustic image based on the electrical signals;

extracting position data regarding the positions of each of a plurality of peaks in the electrical signals that the photoacoustic waves have been converted into, and positive/negative data that indicates whether the peaks are positive or negative;

detecting a signal region sandwiched between a pair of adjacent peaks based on the position data of the peaks in the case that the positive/negative data for the pair of adjacent peaks from among the plurality of peaks are in the order of positive then negative in temporal series; and administering chromatic adjustments to an image region corresponding to the signal region if (i) the signal region includes a flat zone in which signal intensity is constant; and (ii) the positive peak, the flat zone, and the negative peak are detected in this order in temporal series as a correction process that facilitates discrimination of the pair of adjacent peaks and the signal region as being a single tissue system, and wherein the chromatic adjustments include generating mask data which are data for executing a mask process for administering the correction process and overlapping the photoacoustic image and the mask data.

12. A photoacoustic imaging method as defined in claim 11, wherein:
light beams having different wavelengths are output as the measuring light beam; and
the correction process is performed by changing the format of chromatic adjustment for each wavelength of the measuring light beam.

13. A photoacoustic imaging method as defined in claim 11, wherein:
a first generated photoacoustic image is stored;
a first width of a first signal region that the chromatic adjustment was administered on within the first photoacoustic image is compared against a second width of a second signal region, in which chromatic adjustment is to be administered when a second photoacoustic image is to be generated, that corresponds to the first signal region;
judgment is rendered regarding whether the rate of change from the first width to the second width is greater than or equal to a threshold value; and
a predetermined chromatic adjustment is administered to a second image region corresponding to the second signal region according to the result of judgment;
in the case that a plurality of photoacoustic images are continuously imaged.

14. A photoacoustic imaging method as defined in claim 11, wherein:
the position data and the positive/negative data are extracted from the electrical signals after matched addition is administered thereon.

15. A photoacoustic imaging method as defined in claim 11, wherein:
the chromatic adjustments are administered such that the image region corresponding to the signal region sandwiched between the pair of adjacent peaks is emphasized and displayed.

16. A photoacoustic imaging method as defined in claim 15, wherein:
a first generated photoacoustic image is stored;
a first width of a first signal region that the chromatic adjustment was administered on within the first photoacoustic image is compared against a second width of a second signal region, in which chromatic adjustment is to be administered when a second photoacoustic image is to be generated, that corresponds to the first signal region;
judgment is rendered regarding whether the rate of change from the first width to the second width is greater than or equal to a threshold value; and
a predetermined chromatic adjustment is administered to a second image region corresponding to the second signal region according to the result of judgment;
in the case that a plurality of photoacoustic images are continuously imaged.

17. A photoacoustic imaging method as defined in claim 11, wherein:
chromatic adjustments are administered to image regions corresponding to other tissue systems that did not undergo the correction process that enables the image region that underwent the correction process to be discriminated from the other tissue systems.

18. A photoacoustic imaging method as defined in claim 17, wherein:
a first generated photoacoustic image is stored;
a first width of a first signal region that the chromatic adjustment was administered on within the first photoacoustic image is compared against a second width of a second signal region, in which chromatic adjustment is to be administered when a second photoacoustic image is to be generated, that corresponds to the first signal region;
judgment is rendered regarding whether the rate of change from the first width to the second width is greater than or equal to a threshold value; and
a predetermined chromatic adjustment is administered to a second image region corresponding to the second signal region according to the result of judgment;
in the case that a plurality of photoacoustic images are continuously imaged.

19. A photoacoustic imaging method as defined in claim 11, wherein:
the correction process is performed only in a case in which the interval between the two adjacent peaks corresponds to a length of 5 mm or less when converted to a length within living tissue.

20. A photoacoustic imaging method as defined in claim 19, wherein:
a first generated photoacoustic image is stored;
a first width of a first signal region that the chromatic adjustment was administered on within the first photoacoustic image is compared against a second width of a second signal region, in which chromatic adjustment is to be administered when a second photoacoustic image is to be generated, that corresponds to the first signal region;
judgment is rendered regarding whether the rate of change from the first width to the second width is greater than or equal to a threshold value; and
a predetermined chromatic adjustment is administered to a second image region corresponding to the second signal region according to the result of judgment;
in the case that a plurality of photoacoustic images are continuously imaged.

* * * * *